(12) United States Patent
Chen et al.

(10) Patent No.: US 9,339,801 B2
(45) Date of Patent: May 17, 2016

(54) MOLDED CATALYST FOR THE CONVERSION OF METHANOL TO AROMATICS AND PROCESS FOR PRODUCING THE SAME

(71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Xiqiang Chen, Shanghai (CN); Zheming Wang, Shanghai (CN); Jingxian Xiao, Shanghai (CN); Feng Xu, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 271 days.

(21) Appl. No.: 13/939,355

(22) Filed: Jul. 11, 2013

(65) Prior Publication Data
US 2014/0018592 A1      Jan. 16, 2014

(30) Foreign Application Priority Data
Jul. 12, 2012   (CN) .......................... 2012 1 0240007

(51) Int. Cl.
| | |
|---|---|
| C07C 1/20 | (2006.01) |
| C07C 2/66 | (2006.01) |
| B01J 29/48 | (2006.01) |
| C07C 1/22 | (2006.01) |
| B01J 29/40 | (2006.01) |
| B01J 29/44 | (2006.01) |
| B01J 29/46 | (2006.01) |
| B01J 35/10 | (2006.01) |
| C10G 3/00 | (2006.01) |
| B01J 37/00 | (2006.01) |

(52) U.S. Cl.
CPC ............... *B01J 29/48* (2013.01); *B01J 29/405* (2013.01); *B01J 29/44* (2013.01); *B01J 29/46* (2013.01); *B01J 35/1019* (2013.01); *C07C 1/20* (2013.01); *C07C 1/22* (2013.01); *C10G 3/49* (2013.01); *B01J 37/0009* (2013.01); *B01J 2229/18* (2013.01); *B01J 2229/40* (2013.01); *C07C 2529/40* (2013.01); *C10G 2400/30* (2013.01); *Y02P 20/52* (2015.11)

(58) Field of Classification Search
CPC ................................... C07C 2/66; C07C 1/20
USPC .................................................. 585/469, 467
See application file for complete search history.

(56) References Cited

U.S. PATENT DOCUMENTS

| | | | |
|---|---|---|---|
| 4,686,312 A | 8/1987 | Chu et al. | |
| 2002/0038775 A1* | 4/2002 | Sterte | ................. B01J 29/06 208/59 |
| 2002/0099249 A1 | 7/2002 | Drake et al. | |
| 2010/0234658 A1 | 9/2010 | Karim et al. | |

FOREIGN PATENT DOCUMENTS

| | | |
|---|---|---|
| CN | 1880288 A | 12/2006 |
| CN | 1927714 A | 3/2007 |
| CN | 101244969 A | 6/2008 |
| CN | 101550051 A | 10/2009 |

* cited by examiner

*Primary Examiner* — Thuan D Dang
(74) *Attorney, Agent, or Firm* — Finnegan, Henderson, Farabow, Garrett & Dunner LLP

(57) ABSTRACT

The present invention relates to a catalyst for the conversion of methanol to aromatics and the preparation of the same. The catalyst comprising 85 to 99 parts by weight of a ZSM-5 zeolite, 0.1 to 15 parts by weight of element M1, which is at least one selected from the group consisted of Ag, Zn and Ga, and 0 to 5 parts by weight of element M2, which is at least one selected from the group consisted of Mo, Cu, La, P, Ce and Co, wherein the total specific surface area of the catalyst ranges from 350 to 500 m$^2$/g, and the micropore specific surface area ranges from 200 to 350 m$^2$/g. The catalyst has high total specific surface area, micropore specific surface area and micropore volume. Good catalytic activity can be shown from the results of the reaction of aromatics preparation from methanol using the catalyst provided by the present invention.

11 Claims, No Drawings

MOLDED CATALYST FOR THE CONVERSION OF METHANOL TO AROMATICS AND PROCESS FOR PRODUCING THE SAME

The present application claims the priority of Chinese Patent Application No. 201210240007.1, filed on Jul. 12, 2012, which is incorporated herein by reference in its entirety.

TECHNICAL FIELD

The present invention relates to the field of producing aromatics from methanol. More specifically, the present invention relates to a molded catalyst for the conversion of methanol to aromatics and a process for producing the same. In another aspect, the present invention relates to a process for converting methanol to aromatics.

BACKGROUND ART

Aromatics, especially light aromatics such as BTX (benzene, toluene, and xylenes) are important basic organic materials. With the continuous development of global industry and economy in recent years, the demand of aromatics increases continuously. Currently, aromatics mainly come from the naphtha reforming process and the pyrolysis gasoline hydrogenation process, both of which use petroleum as the raw material. According to statistics, aromatics produced by using petroleum as the raw material account for more than 90% of the total aromatics around the world.

However, the cost of aromatics production from petroleum rises sharply due to continuous consumption and increase in price of petroleum resources. Therefore, in the long run, the production of aromatics through the naphtha reforming process and the pyrolysis gasoline hydrogenation process may not meet the growing requirements for aromatics and the cost is higher.

Comparing with petroleum resources, coal resources in the world are more abundant so that they can provide plenty of raw materials for the coal chemical industry. So far, the methanol production process using coal as raw material has been mature. At the same time, excess production capacity of methanol on a global scale has become a serious problem. Therefore, directly converting methanol to produce aromatics may be regarded as a very promising aromatics production line.

U.S. Pat. No. 4,686,312 relates to a catalyst and a process for converting $C_1$-$C_4$ oxygenated hydrocarbons to aromatics. The process is two-stage reactions comprising a primary stage, in which methanol-enriched feedstock is contacted with HZSM-5 zeolite and then converted into an intermediate product containing predominantly aliphatic hydrocarbons, and a secondary stage, in which the intermediate product from the primary stage is contacted with metal modified ZSM-5 zeolite to generate a product rich in aromatics.

US2002/0099249 relates to a process for converting methanol to aromatics and a hybrid catalyst system used. In the process, a feedstock comprising methanol is converted to aromatics by sequentially contacting the feedstock with a first catalyst containing silicoaluminophosphate (SAPO) and then a second catalyst containing metal modified ZSM-5 zeolite. Both of the catalysts contain certain amount of binders.

US2010/0234658 discloses an aromatization catalyst in the type of multi-metal loaded zeolite molecular sieve. The catalyst comprises La and a molecular sieve, a binder, and at least one element selected from Mo, Ce and Cs. In an example of this invention using methanol as the reactant, in the conditions of 450° C., ambient pressure and an WHSV of 9 $h^{-1}$, the yield of aromatics and BTX (methanol weight based) are up to 18.8% and 13.7% respectively, i.e., 43.0% and 31.5% respectively based on carbon.

CN1880288A discloses a process for converting methanol to aromatics and a catalyst used. The catalyst is prepared by mixing a supporter of small particle size ZSM-5 zeolite with a binder (pseudo-boehmite, gamma-alumina or diatomaceous earth) and then molding the mixture, followed by loading active components of Ga and La. The content of the binder in the catalyst may be in a range of 14~34% by weight. In the conditions of 300~460° C., 0.1~5.0 MPa and 0.1~6.0 $h^{-1}$ (WHSV of the liquid feedstock), methanol is contacted with the above catalyst. The yield of aromatics in the formed product is higher than 31% (based on the weight of methanol), i.e. higher than 72% based on carbon. However, this process needs two stages to increase the total yield of aromatics, in which low carbon hydrocarbons obtained from a first stage are subjected to a second reactor to proceed with the aromatization. Thus, this is a rather complex process with many separation steps.

CN101244969A relates to an equipment and a method for a continuous aromatization and catalyst reactivation, specifically relates to a fluidized bed equipment for aromatization of $C_1$~$C_2$ hydrocarbons or methanol and catalyst reactivation and the operational approach thereof. The catalyst used in this invention consists of three components, i.e. a molecular sieve, a metal and a structure stability agent or strengthening agent (corresponding to a binder), wherein the content of the structure stability agent or strengthening agent is more than 20%. It recites in this invention that when an aromatization using methanol as raw material is operated, 97.5% of conversion of methanol, 72% of single pass yield of aromatics (carbon-based) and 55% of BTX selectivity are obtained. Although a high yield of aromatics is obtained, the methanol conversion is low and furthermore the selectivity of BTX that is most valuable in the aromatics is only 55% or so.

As mentioned above, molded catalysts for the conversion of methanol to aromatics reported at present usually consist of a zeolite molecular sieve such as ZSM-5, ZSM-11 or MCM-22, a binder and an active component and a modified component for dehydrogenation. The binder is generally an amorphous oxide such as aluminum oxide, silicon oxide, etc. Since there are certain amounts of binders in these molded catalysts, a portion of pores of the zeolite molecular sieve are blocked up, which inhibits the diffusion of reactants and products and finally results in dropping of activity of the catalyst and selectivity of the subject product. The active component and the modified component for dehydrogenation are usually loaded onto the catalyst by impregnation or mechanical mixing method. However, the active component and the modified component are distributed in homogeneously, most staying on the surface of the catalyst while only a little entering into the inside of the catalyst when they are loaded by using these conventional methods.

In the current situation that the methanol production process using coal as raw material has been mature and the production capacity of methanol may be excess, how to promote the properties of catalysts for converting methanol to aromatics, for example how to promote the activity of the catalysts or simplify the preparation process, may be a main development direction in the field.

SUMMARY OF THE INVENTION

It is an object of this invention to provide a novel molded catalyst for the conversion of methanol to aromatics, which possesses high total specific surface area, micropore specific surface area and micropore volume. The catalyst shows a high reaction activity in the conversion of methanol to aromatics, wherein high yield of aromatics and high yield and selectivity of BTX can be obtained. It is yet another object of this invention to provide a method for making the above-mentioned catalyst.

In addition, a process for producing aromatics from methanol using the above-mentioned catalyst is provided in the present invention.

According to the present invention, a molded catalyst which can be used in the conversion of methanol to aromatics is provided. This catalyst comprises 85 to 99 parts by weight of a ZSM-5 zeolite, 0.1 to 15 parts by weight of element M1, which is at least one selected from the group consisting of Ag, Zn and Ga, and 0 to 5 parts by weight of element M2, which is at least one selected from the group consisting of Mo, Cu, La, P, Ce and Co, wherein the total specific surface area of the catalyst ranges from 350 to 500 $m^2/g$, preferably from 380 to 450 $m^2/g$; the micropore specific surface area of the catalyst ranges from 200 to 350 $m^2/g$, preferably from 260 to 350 $m^2/g$. In addition, the micropore volume of the catalyst may range from 0.08 to 0.20 $cm^3/g$, preferably from 0.12 to 0.20 $cm^3/g$.

The total specific surface area of a catalyst indicates the adsorption and diffusion properties of the catalyst. The higher the total specific surface area of the catalyst used, the higher the adsorption rate of reactants and the desorption rate of products will be, and the higher the reaction activity of the catalyst will be. As defined by International Union of Pure and Applied Chemistry (IUPAC), a micropore refers to a hole having a diameter less than 2 nm, a mesoporous refers to a hole having a diameter between 2~50 nm, and a macropore refers to a hole having a diameter greater than 50 nm. A zeolite molecular sieve generally has a diameter between 0.3~2 nm which falls into the scope of a micropore. Therefore, one of the important indexes to indicate the content of zeolite molecular sieves in a zeolite-type catalyst is the micropore specific surface area of the catalyst. For the same zeolite-type catalyst, the higher the micropore specific surface area is, the higher the content of zeolite in the catalyst will be, the more acid sites necessary for reaction can be provided, and the higher the reaction activity of the catalyst will be. Micropore volume refers to the volume of micropores per unit mass of a catalyst. Similar to the micropore specific surface area, micropore volume can also indicate the zeolite content in a catalyst.

Generally speaking, the total specific surface area of a ZSM-5 zeolite is in the range of 300 to 400 $m^2/g$, and the micropore specific surface area thereof is in the range from 250 to 350 $m^2/g$. The total specific surface area of the molded catalyst, which is obtained by mixing a ZSM-5 zeolite with a binder and subsequently molding the mixture, may be significantly smaller than that of the zeolite. This is mainly resulted from two reasons: for one thing, a portion of the pores of the zeolite are blocked by the binder introduced, which results in a decrease of the micropore specific surface area and total specific surface area; for another, since the specific surface area of a binder, relative to that of a zeolite, is very small and can be almost ignored, the total specific surface area of the catalyst will decrease approximately in a respective ratio with the increasing of the binder. Conventional molded catalysts used in the preparation of aromatics from methanol have a total specific surface area smaller than 300 $m^2/g$ and a micropore specific surface area smaller than 200 $m^2/g$. However, the catalyst provided by the present invention can still maintain a high total specific surface area of 350 to 500 $m^2/g$ as well as a high micropore specific surface area of 200 to 350 $m^2/g$. It can thus advantageously provide more active sites for the reaction and better diffusion properties, which are all beneficial to the improvement of the reaction activity.

In a catalyst, element M1 mainly provides a function of dehydrocyclization. i.e., a process of producing benzene rings from chain hydrocarbons. If the amount of element M1 is lower, the effects of dehydrogenation may be weaker, which results in a decrease in selectivity of aromatics in the product. Contrarily, if the amount of element M1 is too high, the decomposition of methanol will be aggravated, which results in an increase of hydrogen and carbon oxides in the products and a decrease of the selectivity of aromatics. In a preferable embodiment of the present invention, the amount of element M1 in the catalyst provided by the present invention is 1 to 10 parts by weight. Considering that Zn is much more inexpensive than Ga or Ag, in the case that similar reaction activity is requested, Zn may be a preferable option of element M1.

Element M2 mainly serves to improve the hydrothermal stability and inhibit carbon deposition and deactivation of a catalyst. At the same time, proper addition of element M2 can also improve the selectivity of BTX in the product. This is likely due to the modification effect to the pores of the zeolite by element M2, which decreases the production of heavy aromatics. In an embodiment of the present invention, the amount of element M2 in the catalyst may be preferably 0 to 2 parts by weight, and more preferably 0.5 to 2 parts by weight.

The catalyst provided by the present invention contains little if any binders, i.e., the content of binders is 0 to 5 wt. %. In a preferable embodiment of the present invention, the catalyst contains no binders. Many of the conventional catalysts for the conversion of methanol to aromatics contain a binder (the content of binders in a conventional catalyst is usually larger than 15 mass % thereof). The binder is added mainly to improve the strength of the molded catalyst. However, many negative impacts may be brought about at the same time. For example, the pores of molecular sieves may be blocked and the active sites may be covered. As a result, the diffusion of reactants and products may be inhibited, and finally the catalytic activity of the catalyst and the selectivity of the product may be affected. However, the catalyst provided by the present invention contains no binders or hardly contains any binders by placing a dried molded body on the upper dam-board and a template agent and water at the bottom of an autoclave for gas phase crystallizing the molded body (for example by step iii to be described below) to convert most or all of the amorphous silicon aluminum oxide precursor and binders used into a ZSM-5 zeolite. As a result, the above-mentioned defects may be avoided and good catalytic effect may be achieved.

The aromatization of methanol is a reaction of synergy between a Bronsted acid (B acid) and a Lewis acid (L acid). Therefore, more B acid and L acid may be advantageous for the reaction. The B acid of a catalyst is mainly provided by a ZSM-5 zeolite. Moreover, the amount of B acid will decrease with the increase of the molar ratio of Si/Al of the ZSM-5 zeolite and the reaction activity will also decrease, which is indicated by the result of the Examples of the present invention. However, the hydrothermal stability of a ZSM-5 zeolite will gradually decrease with the decrease of the molar ratio of Si/Al thereof. During the process of aromatization of methanol, a large amount of water will be produced. Under the condition that the temperature is high and a large amount of water exists, if the hydrothermal stability of the ZSM-5 zeolite decreases, the framework of the zeolite will collapse, which would result in an irreversible reduction of the B acid and the catalyst would be deactivated permanently. Consequently, after making experimental designs and doing a large numbers of experiments accordingly, it is found that in a preferable catalyst of the present invention, the molar ratio of Si/Al of the ZSM-5 zeolite ranges from 10 to 200:1, preferably from 10 to 100:1, and further preferably from 10 to 50:1.

In the present invention, a method for preparing the above-mentioned catalyst for the conversion of methanol to aromatics is provided. The method comprises: step i: mixing template agent I, an inorganic acid, a silicon source, an aluminum source, water, a soluble compound of element M1 and optionally a soluble compound of element M2 to produce a mixture, gelating the mixture, and then aging and drying the resulted gel to obtain an amorphous silicon aluminum oxide precursor; step ii: mixing the amorphous silicon aluminum oxide precursor obtained in step i with a crystal seed and a binder, molding, and drying the mixture to obtain a molded body; and step iii: crystallizing and then calcinating the molded body obtained from step ii to obtain the catalyst.

The above soluble compounds of elements M1 and M2 are both preferably soluble acids and for salts.

In step i, template agent I is preferably at least one selected from the group consisting of polyethylene glycol, polyethylene oxide, polyoxyethylene polyoxypropylene-polyoxyethylene (P123) and hexadecyl trimethyl ammonium bromide (CTAB).

The inorganic acid used in step i is preferably at least one selected from the group consisting of hydrochloric acid, nitric acid and sulfuric acid.

The silicon source used in step i is preferably at least one selected from the group consisting of tetramethoxysilane, tetraethoxysilane and tetrapropoxysilane.

The aluminum source used in step i is preferably at least one selected from the group consisting of aluminum nitrate, aluminum chloride and aluminum sulfate.

In the mixture of step i, the weight ratio of template agent I:the inorganic acid:the aluminum source:$H_2O$:element M1:element M2:the silicon source is 0.2~1.8:0.05~1.0:0.005~0.085:5~10:0.005~0.3:0~0.025:1, wherein the weight of the aluminum source and that of the silicon source are calculated as the weight of $Al_2O_3$ and $SiO_2$ respectively.

In a specific embodiment of the present invention, in step i, all of the components are mixed at the temperature of 0 to 60° C. to obtain a mixture. The mixture reacts for 0.1 to 10 h under stirring and then is transferred into an airtight container, in which the mixture is gelated at the temperature of 30 to 90° C. An amorphous silicon aluminum oxide precursor is obtained after aging and drying the generated gel.

In step ii, the binder is preferably at least one selected from the group consisting of silica sol, alumina sol, silica white such as fumed silica, and pseudo-boehmite. The crystal seed is preferably selected from HZSM-5 zeolites, Preferably, the molar ratio of Si/Al in the HZSM-5 zeolites is 10~200:1.

In step ii, the weight ratio of the crystal seed:the binder:the amorphous silicon aluminum oxide precursor is 0.001~0.1:0.1~1:1.

In a preferable embodiment of the present invention, a pore-forming agent is further added in step ii, and the pore-forming agent is preferably selected from sesbania powders and/or starch. In the present invention, the added pore-forming agent will be converted into water and carbon dioxide after being calcinated, and will not exist in the catalyst. When pseudo-boehmite is used as the binder in step ii, dilute nitric acid is usually added to improve the adhesive property during the molding process.

In an embodiment of the present invention, the crystallization in step iii is operated at the temperature of 100 to 180° C., by adding template agent II and water at the bottom of an autoclave and adding the molded body obtained from step ii onto the upper dam-board of the autoclave.

In step iii, the weight ratio of template agent II:water:the molded body is 0.01~1:0.5~20:1.

Template agent II is at least one selected from the group consisting of tetrapropylammonium bromide, tetrapropylammonium hydroxide, ethylenediamine, triethylamine, n-propylamine, n-butylamine and hexamethylene diamine.

Usually, the crystallization time in step iii is 0.5 to 8 days. Then the crystallization product is washed, dried at 60 to 130° C. for 2 to 24 h, and then calcinated at 450 to 650° C. for 1 to 8 h.

In another aspect, the present invention also provides a process for converting methanol to aromatics, which comprises the step of contacting methanol which is fed at a weight hourly space velocity (WHSV) of 0.1 to 5.0 $h^{-1}$ with the catalyst as recited above to generate the aromatic product, at the temperature of 350 to 550° C. and the gauge pressure of 0 to 0.5 MPa.

As to the reaction of aromatization, although there is not a unified conclusion about the reaction mechanism at present, many research results indicate that the aromatization of hydrocarbons in a metal-molecular sieve catalyst requires a synergistic action between B acid provided by the molecular sieve and L acid provided by the metal species to achieve a better reaction result. Therefore, the distance between the B acid sites and the metal species is particularly important. When a metal species is loaded to a molecular sieve by a conventional method, for example the impregnation or the mechanical mixing method, most of the metal species remains on the surface of the molecular sieve while only a small part enters inside the molecular sieve. As a result, the synergistic action is limited and thus the reaction activity is lower.

However, in the preparation of the catalyst of the present invention, an amorphous silicon aluminum oxide precursor with a high specific surface area is firstly made and active components (elements M1 and M2) for the aromatization of methanol are introduced during this process. Then the amorphous silicon aluminum oxide precursor and the binder added subsequently are converted into a ZSM-5 zeolite through gas phase crystallization, generating a catalyst substantially without binders and having high total specific surface area, micropore specific surface area and micropore volume. This preparation method brings about some excellent effects. On the one hand, the diffusion of reactants and products is improved and the reaction activity is increased. On the other hand, the dispersity of active components on the molecular sieve is also improved so that the active components are uniformly distributed in the ZSM-5 zeolite, which not only facilitates the synergistic action between B acid and L acid and thus increases the reaction activity, but also promotes the stability of elements M1 and M2 on the catalyst so as to reduce the loss of elements M1 and M2 during the reaction and regeneration processes of the catalyst. In addition, some steps are eliminated in the process of the preparation of the catalyst, including the ammonia ion exchange and loading of elements M1 and M2 after crystallization. The steps of drying and calcination are also reduced. Consequently, the process of the present invention decreases the energy consumption of catalyst preparation.

Generally speaking, the catalyst for the conversion of methanol to aromatics provided by the present invention has high total specific surface area, micropore specific surface area and micropore volume, and uniform dispersion of the active components and thus has good catalytic activity. In the process of the conversion of methanol to aromatics using the catalyst provided by the present invention, high conversion of methanol, high yield of aromatics and high yield and selectivity of BTX can be obtained. For example, with the same Si/Al ratio of the molecular sieve and the same loading of element M1, the catalyst provided by the present invention demonstrates a better reaction activity than that of a common binder-type catalyst, i.e., the yield of aromatics and that of BTX in the product increase by more than 8% respectively.

DETAILED DESCRIPTION OF EMBODIMENTS

The following examples are provided to further illustrate this invention and are not to be considered as unduly limiting the scope of this invention.

Example 1

(1) Preparation and Characterization of the Catalyst 1) 4.0 grams of polyethylene glycol, 8.0 grams of P123, 32.0 grams of hydrochloric acid with a concentration of 1.0 mol/L, 4.0 grams of aluminium nitrate (with a Al content of 13.6 wt % calculated as the weight of $Al_2O_3$), 56.0 grams of tetraethoxysilane (with a Si content of 28.4 wt. % calculated as the weight of $SiO_2$), 8.0 grams of zinc nitrate (with a Zn content of 21.9 wt. %) are uniformly mixed with 50 grams of water and then stirred vigorously at room temperature for 2 h. The formed mixture is then transferred into an airtight container, in which the mixture is gelated at the temperature of 65° C. Sample A1 is obtained after aging the resulted gel for 24 h followed by drying it.

2) 10.0 grams of Sample A1, 0.5 grams of an HZSM-5 zeolite (with a Si/Al molar ratio of 30), 10.0 grams of silica sol (with a Si content of 40.0 wt. % calculated as the weight of $SiO_2$) are mixed and then molded. Sample B1 is obtained after drying the formed product.

3) 10.0 grams of Sample B1 are put onto the upper dam-board of an autoclave, while 10.0 grams of water and 2.0 grams of triethylamine are added into the bottom of the autoclave. Sample B1 is crystallized at 150° C. and the self-generated pressure for 70 h in the autoclave. The resultant is washed, dried at 120° C. for 12 h, and then calcinated at 550° C. for 5 h. A catalyst for conversion of methanol to aromatics referred to as MTA-1 is obtained.

4) The contents of elements M1 and M2 in MTA-1 are tested by plasma emission spectra (ICP). The molar ratio of Si/Al in the framework of the ZSM-5 zeolite is tested by solid-state nuclear magnetic resonance (NMR). The total specific surface area, micropore specific surface area and micropore volume of MTA-1 are measured by nitrogen adsorption-desorption method. All of the results are summarized in Table 1, (2) Reaction for Producing Aromatics from Methanol 10 grams of MTA-1 are added into a reactor. Methanol is fed into the reactor with a WHSV of 1 $h^{-1}$ when the temperature is raised up to 430° C. at the ambient pressure. The results are listed in Table 2.

Examples 2~9

(1) Preparation and Characterization of the Catalysts

Take the same process of step 1) of Example 1, excepting that the zinc nitrate in Example 1 is displaced by the source of elements M1 and M2 as showed in Table 1, catalysts of Examples 2~9, referred to as MTA-2, MTA-3, MTA-4, MTA-5, MTA-6, MTA-7, MTA-8, MTA-9 respectively, are prepared. The physical and chemical properties of them are also listed in Table 1.

(2) Reaction for Producing Aromatics from Methanol

Take the same process of step 2) of Example 1, excepting that MTA-1 is displaced by MTA-2, MTA-3, MTA-4, MTA-5, MTA-6, MTA-7, MTA-8, MTA-9 respectively, to evaluate the reactivity of them. See Table 2.

Example 10

(1) Preparation and Characterization of the Catalyst 1) 120.0 grams of polyethylene oxide, 50.0 grams of P123, 550.0 grams of hydrochloric acid with a concentration of 1.0 mol/L, 52.0 grams of aluminium sulfate (with a Al content of 15.0 wt. % calculated as the weight of $Al_2O_3$), 250.0 grams of tetramethoxysilane (with a Si content of 39.0 wt. % calculated as the weight of $SiO_2$), 70.0 grams of zinc nitrate are mixed with 400.0 grams of water, stirred uniformly and then treated by ultrasonic for 20 min. The formed mixture is then transferred into an airtight container, in which the mixture is gelated at the temperature of 60° C. Sample A10 is obtained after aging the resulted gel for 40 h followed by drying it.

2) 100.0 grams of Sample A10, 10.0 grams of an HZSM-5 zeolite (with a Si/Al molar ratio of 10), 30.0 grams of fumed silica, 4.0 grams of pseudo-boehmite, 28.0 grams of silica sol and a proper amount of dilute nitric acid are mixed together and then molded. Sample B10 is obtained after drying the formed product.

3) 100.0 grams of Sample B10 are put onto the upper dam-board of a autoclave, while 60.0 grams of water and 20.0 grams of hexanediamine are added into the bottom of the autoclave. Sample B10 is crystallized at 170° C. and the self-generated pressure for 60 h in the autoclave. The resultant is washed, dried for 8 h at 130° C., and then calcinated at 600° C. for 3 h. A catalyst for the conversion of methanol to aromatics referred to as MTA-10 is obtained.

4) The physical and chemical properties of MTA-10 are tested by the same methods as those in Example 1. The results are also listed in Table 1.

(2) Reaction for Producing Aromatics from Methanol

Take the same processes of step (2) of Example 1, excepting that MTA-1 is displaced by MTA-10, to evaluate its reactivity. See Table 2.

Example 11

(1) Preparation and Characterization of the Catalyst 1) 8.0 grams of P123, 48.0 grams of sulfuric acid with a concentration of 1.0 mol/L, 2.0 grams of aluminium chloride (with a Al content of 23.1 wt. % calculated as the weight of $Al_2O_3$), 100.0 grams of tetrapropoxysilane (with a Si content of 22.0 wt. % calculated as the weight of $SiO_2$), 10.0 grams of zinc nitrate are mixed with 50 grams of water, stirred for 6 h in the ice-water bath. The formed mixture is then transferred into an airtight container, in which the mixture is gelated at the temperature of 80° C. Sample A11 is obtained after aging the resulted gel for 8 h followed by drying it.

2) 20.0 grams of Sample A11, 0.4 grams of an HZSM-5 zeolite (with a Si/Al molar ratio of 50), 20.0 grams of silica sol and a proper amount of water are mixed together and then molded. Sample B11 is obtained after drying the formed product.

3) 10.0 grams of Sample B11 are put onto the upper damboard of an autoclave, while 10.0 grams of water and 3.0 grams of n-butylamine are added into the bottom of the autoclave. Sample B11 is crystallized at 130° C. and the self-generated pressure for 96 h in the autoclave. The resultant is washed, dried for 18 h at 110° C., and then calcinated at 550° C. for 4 h. A catalyst for the conversion of methanol to aromatics referred to as MTA-11 is obtained.

4) The physical and chemical properties of MTA-11 are tested by the same methods as those in Example 1. The results are also listed in Table 1.

(2) Reaction for Producing Aromatics from Methanol

Take the same process of step (2) of Example 1, excepting that MTA-1 is displaced by MTA-11, to evaluate its reactivity. See Table 2.

Example 12

(1) Preparation and Characterization of the Catalyst 1) 4.0 grams of CTAB, 4.0 grams of P123, 40.0 grams of tetramethoxysilane, 0.8 grams of aluminium nitrate, 5.0 grams of zinc nitrate, 32.0 grams of hydrochloric acid with a concentration of 1.0 mol/L are mixed with 70.0 grams of water, stirred for 4 h at room temperature. The formed mixture is then transferred into an airtight container, in which the mixture is gelated at the temperature of 70° C. Sample A12 is obtained after aging the resulted gel for 24 h followed by drying it.

2) 10.0 grams of Sample A12, 0.5 grams of an HZSM-5 zeolite (with a Si/Al molar ratio of 175), 8.0 grams of silica sol and a proper amount of water are mixed together and then molded. Sample B12 is obtained after drying the formed product.

3) 10.0 grams of Sample B12 are put onto the upper damboard of an autoclave, while 6.0 grams of water and 1.5 grams of tetrapropylammonium hydroxide are added into the bottom of the autoclave. Sample B12 is crystallized at 150° C. and the self-generated pressure for 36 h in the autoclave. The resultant is washed, dried for 24 h at 80° C., and then calcinated at 500° C. for 6 h. A catalyst for the conversion of methanol to aromatics referred to as MTA-12 is obtained.

4) The physical and chemical properties of MTA-12 are tested by the same methods as those in Example 1. The results are also listed in Table 1.

(2) Reaction for Producing Aromatics from Methanol

Take the same process of step (2) of Example 1, excepting that MTA-1 is displaced by MTA-12, to evaluate its reactivity. See Table 2.

Example 13

(1) Preparation and Characterization of the Catalyst 1) 8.0 grams of polyethylene glycol, 20.0 grams of P123, 60.0 grams of nitric acid with a concentration of 1 mol/L, 2.5 grams of aluminium nitrate, 100.0 grams of tetraethoxysilane, 30.0 grams of zinc nitrate are mixed with 100.0 grams of water and then stirred vigorously for 4 h at room temperature. The formed mixture is then transferred into an airtight container, in which the mixture is gelated at the temperature of 70° C. Sample A13 is obtained after aging the resulted gel for 30 h followed by drying it.

2) 10.0 grams of Sample A13, 1.0 gram of an HZSM-5 zeolite (with a Si/Al molar ratio of 100), 8.0 grams of silica sol and a proper amount of water are mixed and then molded. Sample B13 is obtained after drying the formed product.

3) 10.0 grams of Sample B13 are put onto the upper damboard of an autoclave, while 8.0 grams of water and 2.0 grams of n-propylamine are added into the bottom of the autoclave. Sample B13 is crystallized at 150° C. and the self-generated pressure for 65 h in the autoclave. The resultant is washed, dried at 100° C. for 16 h, and then calcinated at 550° C. for 4 h. A catalyst for the conversion of methanol to aromatics referred to as MTA-13 is obtained.

4) The physical and chemical properties of MTA-13 are tested by the same methods as those in Example 1. The results are also listed in Table 1.

(2) Reaction for Producing Aromatics from Methanol

Take the same process of step (2) of Example 1, excepting that MTA-1 is displaced by MTA-13, to evaluate its reactivity. See Table 2

Example 14

(1) Preparation and Characterization of the Catalyst 1) 10.0 grams of Sample A13 obtained from Example 13, 0.5 grams of an HZSM-5 zeolite (with a Si/Al molar ratio of 100), 8.0 grams of silica sol and a proper amount of water are mixed and then molded. Sample B14 is obtained after drying the formed product.

2) 10.0 grams of Sample B14 are put onto the upper damboard of an autoclave, while 10.0 grams of water and 2.0 grams of tetrapropylammonium hydroxide are added into the bottom of the autoclave. Sample B14 is crystallized at 170° C. and the self-generated pressure for 48 h in the autoclave. The resultant is washed, dried at 110° C. for 20 h, and then calcinated at 560° C. for 3 h. A catalyst for the conversion of methanol to aromatics referred to as MTA-14 is obtained.

3) The physical and chemical properties of MTA-14 are tested by the same methods as those in Example 1. The results are also listed in Table 1.

(2) Reaction for Producing Aromatics from Methanol

Take the same process of step (2) of Example 1, excepting that MTA-1 is displaced by MTA-14, to evaluate its reactivity. See Table 2.

Comparative Example 1

(1) Preparation and Characterization of the Catalyst 1) 7.0 grams of ethanediamine, 90.0 grams of silica sol, 2.0 grams of sodium metaaluminate, 6.0 grams of sodium hydroxide are mixed uniformly with 250.0 grams of water. The formed mixture is then transferred into a stainless autoclave, in which the mixture is crystallized at 150° C. and the self-generated pressure for 70 h. Sample A15 is obtained after washing and then drying the resultant.

2) 20.0 grams of Sample A15, 7.0 grams of pseudo-boehmite and a proper amount of dilute nitric acid are mixed and then molded. Sample B15 is obtained after drying and calcinating the formed product.

3) 20.0 grams of Sample B15 are added to 100.0 grams of ammonium nitrate solution with a concentration of 5.0 wt. % and the mixture is subjected to a treatment of heating reflux at 90° C. for 2 h. The sample is washed with water and the foregoing step is repeated for 3 times. The sample is dried and calcinated to obtain Sample C15.

4) 10.0 grams of Sample C15 are mixed with 8.0 grams of zinc nitrate solution (with a Zn content of 4.0 wt. %) and then the mixture is dried at 130° C. for 8 h followed by calcination at 600° C. for 3 h. A catalyst for the conversion of methanol to aromatics referred to as MTA-15 is obtained.

5) The physical and chemical properties of MTA-15 are tested by the same methods as those in Example 1. The results are also listed in Table 1.

(2) Reaction for Producing Aromatics from Methanol

Take the same process of step (2) of Example 1, excepting that MTA-1 is displaced by MTA-15, to evaluate its reactivity. See Table 2.

Comparative Example 2

(1) Preparation and Characterization of the Catalyst 1) 6.0 grams of tetrapropylammonium bromide, 100.0 grams of silica sol, 2.0 grams of aluminum sulfate, 6.0 grams of sodium hydroxide, and 6.0 grams of sodium chloride are uniformly mixed with 240.0 grams of water. The formed mixture is then transferred into a stainless autoclave, in which the mixture is crystallized at 170° C. and the self-generated pressure for 48 h. Sample A16 is obtained after washing and then drying the resultant.

2) 20.0 grams of Sample A16, 20.0 grams of silica sol and a proper amount of water are mixed and then molded. Sample B16 is obtained after drying and calcinating the formed product.

3) 20.0 grams of Sample B16 are added to 60.0 grams of ammonium chloride solution with an concentration of 8.0 wt. % and the mixture is then subjected to a treatment of heating reflux at 90° C. for 3 h. The sample is washed with water and the foregoing steps are repeated 3 times. The sample is dried and calcinated to obtain Sample C16.

4) 10.0 grams of Sample C16 are mixed with 8.0 grams of zinc nitrate solution (with a Zn content of 4.0 wt. %) and then the mixture is dried at 120° C. for 12 h followed by calcination at 550° C. for 5 h. A catalyst for the conversion of methanol to aromatics referred to as MTA-16 is obtained.

5) The physical and chemical properties of MTA-16 are tested by the same methods as those in Example 1. The results are also listed in Table 1.

(2) Reaction for Producing Aromatics from Methanol

Take the same process of step (2) of Example 1, excepting that MTA-1 is displaced by MTA-16, to evaluate its reactivity. See Table 2, Examples 15~25

The reactivity of catalyst MTA-10 is evaluated in different reaction conditions (see Table 3) and the results are shown in Table 3,

TABLE 1

| Examples | Catalysts | Si/Al molar ratio of the ZSM-5 zeolite | Element M1 (wt. %) | Element M2 (wt. %) | Total specific surface area ($m^2/g$) | Micropore specific surface area ($m^2/g$) | Micropore volume ($cm^3/g$) |
|---|---|---|---|---|---|---|---|
| Example 1 | MTA-1 | 30 | Zn, 3.0 | / | 429 | 299 | 0.139 |
| Example 2 | MTA-2 | 28 | Ag, 1.0 | / | 433 | 302 | 0.139 |
| Example 3 | MTA-3 | 31 | Ga, 2.0 | / | 430 | 297 | 0.139 |
| Example 4 | MTA-4 | 31 | Zn, 3.0 | Mo, 1.0 | 413 | 289 | 0.138 |
| Example 5 | MTA-5 | 33 | Zn, 3.0 | Cu, 2.0 | 406 | 286 | 0.138 |
| Example 6 | MTA-6 | 29 | Zn, 3.0 | La, 1.0 | 414 | 289 | 0.138 |
| Example 7 | MTA-7 | 29 | Zn, 3.0 | P, 1.0 | 407 | 280 | 0.136 |
| Example 8 | MTA-8 | 30 | Zn, 3.0 | Ce, 1.0 | 420 | 291 | 0.137 |
| Example 9 | MTA-9 | 29 | Ag, 1.0 | Co, 1.0 | 420 | 294 | 0.138 |
| Example 10 | MTA-10 | 10 | Zn, 3.0 | / | 445 | 305 | 0.142 |
| Example 11 | MTA-11 | 50 | Zn, 3.0 | / | 388 | 271 | 0.128 |
| Example 12 | MTA-12 | 175 | Zn, 3.0 | / | 447 | 326 | 0.157 |
| Example 13 | MTA-13 | 100 | Zn, 10.0 | / | 419 | 291 | 0.137 |
| Example 14 | MTA-14 | 100 | Zn, 10.0 | / | 428 | 315 | 0.143 |
| Comparative Example 1 | MTA-15 | 10 | Zn, 3.0 | / | 225 | 168 | 0.074 |
| Comparative Example 2 | MTA-16 | 50 | Zn, 3.0 | / | 207 | 149 | 0.068 |

TABLE 2

| Examples | Catalysts | Conversion of methanol (%) | Yield of aromatics (carbon-based, %) | Yield of BTX (carbon-based, %) | Selectivity of BTX (%) |
|---|---|---|---|---|---|
| Example 1 | MTA-1 | 99.9 | 62.4 | 51.2 | 82.0 |
| Example 2 | MTA-2 | 99.9 | 63.7 | 52.6 | 82.6 |
| Example 3 | MTA-3 | 99.9 | 58.3 | 47.6 | 81.6 |
| Example 4 | MTA-4 | 99.9 | 55.6 | 46.1 | 82.9 |
| Example 5 | MTA-5 | 99.9 | 57.9 | 47.8 | 82.6 |
| Example 6 | MTA-6 | 99.9 | 61.0 | 50.8 | 83.3 |
| Example 7 | MTA-7 | 99.9 | 60.8 | 51.3 | 84.4 |
| Example 8 | MTA-8 | 99.9 | 59.7 | 49.0 | 82.1 |
| Example 9 | MTA-9 | 99.9 | 63.2 | 52.8 | 83.5 |
| Example 10 | MTA-10 | 99.9 | 65.9 | 54.4 | 82.5 |
| Example 11 | MTA-11 | 99.9 | 55.7 | 45.0 | 80.8 |
| Example 12 | MTA-12 | 99.8 | 51.7 | 41.4 | 80.1 |
| Example 13 | MTA-13 | 99.9 | 53.7 | 42.9 | 79.9 |
| Example 14 | MTA-14 | 99.9 | 58.4 | 46.0 | 78.8 |
| Comparative Example 1 | MTA-15 | 99.9 | 51.2 | 39.5 | 77.1 |
| Comparative Example 2 | MTA-16 | 99.9 | 46.3 | 35.4 | 76.5 |

Comparing Example 10 with Comparative Example 1, in the case that the kind and content of element M1 and the Si/Al molar ratio of the ZSM-5 zeolite molecular sieve are all the same, the yield of aromatics and the yield of BTX and the selectively of BTX of Example 10 are respectively 65.9%, 54.4% and 82.5%, which are all higher than those of Comparative Example 1. The comparison between Example 11 and Comparative Example 2 indicates a similar conclusion. In conclusion, the catalysts produced by the process of the present invention possess better reaction activity. The reaction for producing aromatics from methanol using the catalysts provided by this invention achieves better results, e.g., higher yield of aromatics and higher yield and selectivity of BTX.

Table 3 lists the reaction results of the conversion of methanol to aromatics using catalyst MTA-10 in different reaction process conditions. It can be seen that, though the yield of aromatics descends to a certain degree with the decrease of temperature, the increase of pressure or the increase of WHSV, the conversion of methanol is still more than 99%. This also proves a high activity of the catalyst of this invention.

TABLE 3

| Examples | Temperatures (° C.) | Gauge pressure (MPa) | WHSV (h$^{-1}$) | Conversion of methanol (%) | Yield of aromatics (carbon-based, %) | Yield of BTX (carbon-based, %) |
|---|---|---|---|---|---|---|
| Example 15 | 370 | 0 | 1.0 | 99.9 | 58.0 | 49.8 |
| Example 16 | 420 | 0 | 1.0 | 99.9 | 64.7 | 53.2 |
| Example 17 | 470 | 0 | 1.0 | 99.9 | 66.2 | 55.8 |
| Example 18 | 520 | 0 | 1.0 | 99.9 | 67.4 | 54.2 |
| Example 19 | 420 | 0.1 | 1.0 | 99.9 | 62.4 | 51.2 |
| Example 20 | 420 | 0.3 | 1.0 | 99.9 | 60.1 | 48.6 |
| Example 21 | 420 | 0.5 | 1.0 | 99.9 | 56.4 | 45.1 |
| Example 22 | 420 | 0 | 0.1 | 99.9 | 67.8 | 56.2 |
| Example 23 | 420 | 0 | 0.5 | 99.9 | 65.3 | 54.7 |
| Example 24 | 420 | 0 | 2.0 | 99.8 | 61.2 | 49.8 |
| Example 25 | 420 | 0 | 4.0 | 99.7 | 56.3 | 45.2 |

The catalysts in the above examples and comparative examples are all molded catalysts. From Table 1, it can be seen that the catalysts provided by this invention have high total specific surface area, micropore specific surface area and micropore volume. For example, catalysts MTA-1 to MTA-10 all have a total specific surface area of higher than 350 m$^2$/g, and most of them are higher than 400 m$^2$/g. By contrast, the total specific surface areas of the catalysts in Comparative Example 1 and Comparative Example 2 are only 225 m$^2$/g and 207 m$^2$/g respectively. The micropore specific surface areas of catalyst MTA-1 to MTA-10 are all higher than 270 m$^2$/g. By contrast, the micropore specific surface areas of the catalysts in Comparative Example 1 and Comparative Example 2 are respectively 168 m$^2$/g and 149 m$^2$/g only. Moreover, the micropore volume of the catalysts in the examples is also significantly higher than that of the catalysts in the comparative examples.

In addition, from the original raw materials to the catalyst finally obtained, there are 3 drying steps and 1 calcination steps in process of the present invention, while there are 4 steps of drying and 3 steps of calcination in the process of a conventional method. It means that, the present invention has a significant advantage in the aspects of energy-saving and cost-educing.

What is claimed is:

1. A process for converting methanol to aromatics comprising contacting methanol with a molded catalyst to convert methanol to aromatics at a temperature ranging from 350 to 550° C. and under a pressure ranging from 0 to 0.5 MPa, wherein the methanol is fed at a weight hourly space velocity ranging from 0.1 to 5.0 h$^{-1}$, wherein the molded catalyst comprises 85 to 99 parts by weight of a ZSM-5 zeolite, 0.1 to 15 parts by weight of at least one element M1 selected from Ag, Zn and Ga, and 0 to 5 parts by weight of at least one element M2 selected from Cu, La, P, Ce and Co, and wherein the total specific surface area of the catalyst ranges from 350 to 500 m²/g, and the micropore specific surface area of the catalyst ranges from 200 to 350 m²/g.

2. The process according to claim herein the specific surface area of the catalyst ranges from 380 to 450 m²/g.

3. The process according to claim 1, wherein the micropore specific surface area ranges from 260 to 350 m²/g.

4. The process according to claim 1, wherein the micropore volume of the catalyst ranges from 0.08 to 0.20 cm³/g.

5. The process according to claim 1, wherein the amount of the at least one element M1 ranges from 1 to 10 parts by weight and the amount of the at least one element M2 ranges from 0 to 2 parts by weight.

6. The process according to claim 1, wherein the catalyst contains from 0 to 5 ma of a binder.

7. The process according to claim 1, wherein the molar ratio of Si to Al in the ZSM-5 zeolite is in the range of 10 to 200:1.

8. The process according to claim 1, wherein the molar ratio of Si to Al in the ZSM-5 zeolite is in the range of 10 to 100:1.

9. The process according to claim 1, wherein the micropore volume of the catalyst ranges from 0.12 to 0.20 cm³/g.

10. The process according to claim 1, wherein the catalyst contains no binder.

11. The process according to claim 1, wherein the molar ratio of Si to Al in the ZSM-5 zeolite is in the range of 10 to 50:1.

* * * * *